US006977292B2

(12) United States Patent
Botti et al.

(10) Patent No.: US 6,977,292 B2
(45) Date of Patent: Dec. 20, 2005

(54) NUCLEOPHILE-STABLE THIOESTER GENERATING COMPOUNDS, METHODS OF PRODUCTION AND USE

(75) Inventors: Paolo Botti, Piacenza (IT); James A. Bradburne, Redwood City, CA (US); Stephen B. H. Kent, San Francisco, CA (US)

(73) Assignee: Gryphon Therapeutics, South San Francisco, CA (US)

( * ) Notice: Subject to any disclaimer, the term of this patent is extended or adjusted under 35 U.S.C. 154(b) by 288 days.

(21) Appl. No.: 10/332,454

(22) PCT Filed: Aug. 30, 2001

(86) PCT No.: PCT/US01/41938

§ 371 (c)(1),
(2), (4) Date: Jan. 9, 2003

(87) PCT Pub. No.: WO02/18417

PCT Pub. Date: Mar. 7, 2002

(65) Prior Publication Data

US 2003/0149234 A1 Aug. 7, 2003

Related U.S. Application Data

(63) Continuation of application No. PCT/US01/41938, filed on Aug. 30, 2001.
(60) Provisional application No. 60/229,295, filed on Sep. 1, 2000.

(51) Int. Cl.$^7$ ............................................. C07K 1/04
(52) U.S. Cl. ...................... 530/333; 530/334; 530/345; 554/101; 560/1
(58) Field of Search ................................ 530/333, 334, 530/345; 554/101; 560/1

(56) References Cited

U.S. PATENT DOCUMENTS

| | | | | |
|---|---|---|---|---|
| 5,478,808 A | * | 12/1995 | Tanida et al. ................. | 514/15 |
| 5,478,809 A | * | 12/1995 | Tanida et al. ................. | 514/16 |
| 5,506,267 A | * | 4/1996 | Aono et al. .................. | 514/616 |
| 5,753,764 A | * | 5/1998 | Boutevin et al. ............. | 525/287 |
| 5,854,389 A | | 12/1998 | Kent et al. ................... | 530/334 |
| 6,307,018 B1 | * | 10/2001 | Kent et al. ................... | 530/333 |
| 6,326,468 B1 | * | 12/2001 | Canne et al. ................. | 530/333 |
| 6,429,223 B1 | * | 8/2002 | Lai et al. ..................... | 514/411 |
| 6,458,908 B1 | * | 10/2002 | Imai et al. ................... | 526/259 |
| 6,476,190 B1 | * | 11/2002 | Kent et al. ................... | 530/333 |
| 6,552,167 B1 | | 4/2003 | Rose ............................ | 530/326 |
| 6,699,862 B1 | * | 3/2004 | Goldstein et al. ........... | 514/235.2 |

FOREIGN PATENT DOCUMENTS

| WO | WO 96/34878 | 11/1996 |
|---|---|---|
| WO | WO 98/28434 | 7/1998 |

OTHER PUBLICATIONS

Auriault, C. et al., "Epitopic Characterization and Vaccinal Potential of Peptides Derived from a Major Antigen of Schistosoma mansoni," (1991) *Peptide Res.* 4, 6–11.

Shin et al., Fmoc–Based Synthesis of Peptide–Alpha Thioesters: Application to the Total Chemical Synthesis of a Glycoprotein by Native Chemical Ligation, *J. Amer. Chem. Soc.* (1999) 121:11684–11689.

Botti, P. et al., "Native Chemical Ligation Using Removable N.alpha –(1–phenyl–2–mercaptoethyl) Auxillaries," *Tetrahedron Letters* 42, 1831–1833 (2001).

Canne et al., "A General Method for the Synthesis of Thioester Resin Linkers for Use in the Solid Phase Synthesis of Peptide–alpha–Thioacids," *Tetrahedron Lett.* (1995) 36:1217–1220.

Canne L.E. et al., "Solid Phase Protein Synthesis by Chemical Ligation of Unprotected Peptide Segments in Aqueous Solution," *Peptides: Frontiers of Peptide Science, Proceedings of the American Peptide Symposium*, 15th, Nashville, Tennessee, Jun. 14–19, 1997, 301–302 (1999).

Clippingdale et al., "Peptide Thioester Preparation by Fmoc Solid Phase Peptide Synthesis for Use in Native Chemical Ligation," *J. Peptide Sci.* (2000) 6: 225–234.

Davies M. et al., "C–terminal modifizierte Peptide und Peptidbibliotheken—ein neuer Zugang zu Peptiden vom,, anderen Ende her**" (1997) *Angew. Chem.* 109:1135–1138.

Davies M. et al., "Screening an Inverted Peptide Library in Water with a Guanidinium–Based Tweezer Receptor," (1998) *J.Org. Chem.* 8696–8703.

Dawson et al., "Synthesis of Chemokines by Native Chemical Ligation," *Methods Enzymol.* (1997) 287:34–45.

Dawson et al., "Synthesis of Native Proteins By Chemical Ligation," *Ann. Rev. Biochem* (2000) 69:923–960.

Dawson, P.E. et al. Synthesis of Proteins by Native Chemical Ligation, Science 266, 776–779 (1994).

(Continued)

*Primary Examiner*—David Lukton
(74) *Attorney, Agent, or Firm*—Jeffrey I. Auerbach; Berenato, White & Stavish

(57) ABSTRACT

The invention is directed to nucleophile-stable thioester generating compounds comprising a carboxyester thiol. The compounds have wide applicability in organic synthesis, including the generation of peptide-, polypeptide- and other polymer-thioesters. The invention is particularly useful for generating activated-thioesters from precursors that are made under conditions in which strong nucleophiles are employed, such as peptides or polypeptides made using Fmoc SPPS, as well as multi-step ligation or conjugation schemes that require (or benefit from the use of) compatible selective approaches for directing a specific ligation or conjugation reaction of interest.

23 Claims, 4 Drawing Sheets

OTHER PUBLICATIONS

Feugeas et al., "Chimie Organique.—Préparation de composés thioalcoxy á structure trivalente mixte. Note (*) de MM. Claude Feugeas et Daniel Olschwang, transmise par M. Henri Normant.," *C.R. Acad Sci., Paris, Ser.C* (1968) 266(20):1506–1507.

Gaertner et al., "Site Specific Attachment of Functionalized Poly(ethylene glycol) to the Amino Terminus of Proteins," *Bioconjug. Chem.* (1996) 7(1):38–44.

Hackeng et al., "Protein synthesis by native chemical ligation: expanded scope by using straightforward methodology," *Proc Natl Acad Sci U S A*. Aug. 31, 1999;96(18):10068–73.

Honma et al., "Studies on Glycosylation A S–Glycosylation by use of stannic Chloride," *Chem. Pharm. Bull.* (1976) 24(4):818–820.

Ingenito et al., "Solid Phase Synthesis of Peptide C–Terminal Thioesters by Fmoc/t–Bu Chemistry," *JACS* (1999) 121(49):11369–11374.

Kent S., et al., "Determining the Structure of HIV–1 Protease," *Science* 288, 1590 (2000).

Kent, S.B.H. "Chemical Synthesis of Peptides And Proteins," (1988) *Ann. Rev. Biochem.* 57, 957–984.

Kochendoerfer G.G. et al., "Total Chemical Synthesis of the Integral Membrane Protein Influenza A Virus M2: Role of Its C–Terminal Domain in Tetramer Assembly," *Biochemistry* 38, 11905–11913 (1999).

Kochendoerfer, G.G. et al. "Chemical Protein Synthesis Methods in Drug Discovery," *Current Opinion in Drug Discovery & Development* 4, 205–214 (2001).

Kochendoerfer, G.G. et al. "Total Chemical Synthesis of a 27 kDa TASP Protein Derived from the MscL Ion Channel of M. Tuberulosis by Ketoxime–forming Ligation," *Bioconjugate Chemistry* 13, 474–480 (2002).

Kochendoerfer, G.G. et al., "Chemical Protein Synthesis," *Current Opinion in Chemical Biology* 3, 665–671 (1999).

Low D.W. et al., "Rational Fine–Tuning of the Redox Potentials in Chemically Synthesized Rubredoxins," *Journal of the American Chemical Society* 120, 11536–11537 (1998).

Low, D.W. et al., "Backbone–engineered High–potential Iron Proteins: Effects of Active–Site Hydrogen Bonding on Reduction Potential," *Journal of the American Chemical Society* 122, 11039–11040 (2000).

Low, D.W. et al., "Total Synthesis of Cytochrome b562 by Native Chemical Ligation Using a Removable Auxiliary," *Proceedings of the National Academy of Sciences of the United States of America* 98, 6554–6559 (2001).

Lu W. et al. "Total Chemical Synthesis of Bovine Pancreatic Trypsin Inhibitor by Native Chemical Ligation," *FEBS Letters* 429, 31–35 (1998).

Posnett, D. N. et al., "A Novel Method for Producing Anti–Peptide Antibodies," (1988) *J. Biol. Chem.* 263, 1719–1725.

Robson B., et al. "Doppelganger Proteins as Drug Leads," *Nature Biotechnology* 14, 892–893 (1996).

Rose et al., "Stepwise Solid–Phase Synthesis of Polyamides As Linkers," *J. Am. Chem. Soc.* Aug. 4, 1999, 121:7034–7038.

Rose, et al., "Facile Synthesis of Homogeneous Artificial Proteins," *J. Amer. Chem. Soc.* (1994) 116:30–34.

Rose, K. et al., "Natural Peptides as Building Blocks for the Synthesis of Large Protein–like Molecules with Hydrazone and Oxime Linkages," *Bioconjugate Chem.* (1996) 7:552–556.

Shao Y.et al., "A Novel Method to Synthesize Cyclic Peptides," *Tetrahedron Letters* 39, 3911–3914 (1998).

Shao Y. et al., "Protein Splicing: Occurrence, Mechanisms, and Related Phenomena," *Chemistry & Biology* 4, 187–194 (1997).

Siani M.A. et al., "Rapid Modular Total Chemical Synthesis of Proteins Based on Genome Sequence Data," *Peptides: Frontiers of Peptide Science, Proceedings of the American Peptide Symposium*, 15th, Nashville, Tennessee, Jun. 14–19, 1997, 643–644 (1999).

Tam et al. "Methionine Ligation Strategy in the Biomimetic Synthesis of Parathyroid Hormones," *Biopolymers*, 1998, vol. 46, pp. 319–327.

Tam, J. P., "Synthetic peptide vaccine design: Synthesis and properties of a high–density multiple antigenic peptide system," (1988) *Proc. Natl. Acad. Sci. U.S.A.* 85, 5409–5413.

Wade, J.D. et al., "Solid Phase Peptide Synthesis Recent Advances and Applications," *Australas Biotechnol.* (1993) 3(6):322–6.

Wells et al., "Solid–Phase Dendrimer Synthesis," *Biopolymers* (1998) 47:381–396.

Wilken J. et al., "Chemical Protein Synthesis," *Current Opinion in Biotechnology* 9, 412–426 (1998).

Wilken J. et al., "Rational Development of an Anti–HIV Protein Active at Low Picomolar Concentrations," *Peptides for the New Millennium, Proceedings of the American Peptide Symposium*, 16th, Minneapolis, Minnesota, Jun. 26–Jul. 1, 1999, 513–515 (2000).

Zlotnik et al., "Recent Advances in Chemokines and Chemokine Receptors," *Critical Rev. Immunology* (1999) 19(1):1–4.

Zhang, et al., "Preparation of functionally active cell–permeable peptides by single–step ligation of two peptide modules," *Proc Natl Acad Sci USA*. Aug. 4, 1998;95(16):9184–9.

Zlatkine et al., "Retargeting of cytosolic proteins to the plasma membrane by the Lck protein tyrosine kinase dual acylation motif," *J. Cell Sci.* (1997) 110:673–679.

Zlotnik et al., "Recent Advances in Chemokines and Chemokine Receptors," *Critical Rev. Immunology* (1999) 19(1):1–4.

* cited by examiner

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Phe Lys Leu Ala Gly
1               5
```

```
<210> SEQ ID NO 2
<211> LENGTH: 13
<212> TYPE: PRT
<213> ORGANISM: Artificial
<220> FEATURE:
<223> OTHER INFORMATION: Synthetic

<400> SEQUENCE: 2

Cys Ala Arg His Thr Val His Gln Arg His Leu Phe Gly
1               5                   10
```

NUCLEOPHILE-STABLE THIOESTER GENERATING COMPOUNDS, METHODS OF PRODUCTION AND USE

CROSS REFERENCE TO RELATED APPLICATIONS

This application is a continuation of International Patent Application No. PCT/US01/41938, filed on Aug. 30, 2001, and a continuation-in-part of U.S. Provisional Patent Application Ser. No. 60/229,295, filed on Sep. 1, 2000, both of which applications are herein incorporated by reference.

TECHNICAL FIELD

The invention relates to nucleophile-stable thioester generating compounds, methods of their production and use.

BACKGROUND

Thioesters represent an important class of molecules that readily react with nucleophiles. Thioesters are particularly useful for conjugation and chemoselective ligation reactions. Chemical ligation involves the chemoselective covalent linkage of a first chemical component to a second chemical component. Unique, mutually-reactive functional groups present on the first and second components can be used to render the ligation reaction chemoselective. For example, thioesters are commonly used to direct the chemoselective chemical ligation of peptides and polypeptides. Several different thioester-mediated chemistries have been utilized for this purpose, such as native chemical ligation (Dawson, et al., Science (1994) 266:776–779; Kent, et al., WO 96/34878; Kent, et al., WO 98/28434).

Unfortunately, conventional conditions under which peptide and other thioesters are prepared (Hojo, et al. Pept. Chem. (1992), Volume Date 1991, 29th pp. 115–20; Canne, et al. Tetrahed. Letters (1995) 36: 1217–20; Hackeng, et al. Proc Natl Acad Sci USA. (1999) 96: 10068–73) and in some instances used, are limited to non-nucleophilic synthetic strategies. For example, a problem faced when attempting to make thioester-activated peptides using Nα-9-fluorenylmethyloxycarbonyl ("Fmoc")-based peptide synthesis is the unwanted destruction of the thioester moiety by strong nucleophiles such as piperidine or piperidine-generated hydroxide ions during synthesis of the peptide. This is a significant problem since the preferred reagent employed to remove Nα-Fmoc groups in each cycle of Fmoc-based organic synthesis contains piperidine. Piperidine like other strongly basic or nucleophilic compounds (hereinafter "nucleophiles") destroys the thioester component of the peptide, rendering it useless for subsequent thioester-mediated reactions.

Several attempts have been made to address this problem. Clippingdale et al. (J. Peptide Sci. (2000) 6: 225–234) have used a non-nucleophilic base to remove Nα-Fmoc groups of peptides made using Fmoc-based Solid Phase Peptide Synthesis ("SPPS"). This approach has several problems, including generation of unwanted deletions, side-products, and requirement for backbone protection strategies. Other groups, including, Bertozzi et al. (J. Amer. Chem. Soc. (1999) 121:11684–11689) and Pessi et al. (Journal of the American Chemical Society; 1999; 121: 11369–11374.), have reported adapting Fmoc SPPS in combination with a 'Kenner' safety-catch linker, which is stable to nucleophiles until the linker has been alkylated, to produce a fully protected peptide-thioester in solution. A drawback of this approach is the poor solubility properties of protected peptides in solution. Other drawbacks of this approach include side reactions inherent to the method, such as the formation of unwanted alkylated byproducts when the linker is alkylated to render it labile, and thus it is impractical for many applications. Similar frustration has been experienced in nucleophilic-based synthesis schemes for molecules other than peptides, such as small organic molecules.

Accordingly, what is needed is a universal and robust system for generating nucleophile-stable thioester-generating compounds and compositions compatible with organic or aqueous reaction conditions for use in various organic synthesis strategies, and conjugation and chemoselective ligation reactions that employ thioester-mediated reactions. The present invention addresses this and other needs.

SUMMARY OF THE INVENTION

The invention is directed to methods and compositions related to nucleophile-stable thioester generating compounds. In one embodiment, the invention is directed to a nucleophile-stable orthothioloester of the formula X—C(OR')$_2$—S—R, where X is a target molecule of interest optionally comprising one or more nucleophile-labile protecting groups, R is any group compatible with the orthothio moiety —C(OR')$_2$—S—, and R' is a nucleophile-stable protecting group that is removable under non-nucleophilic conditions. In another embodiment, the invention is directed to a nucleophile-stable carboxyester alkyl thiol of the formula X—C(O)—O—CH(R")—(CH$_2$)$_n$—S—R''', where X is a target molecule of interest comprising one or more nucleophile-labile protecting groups, R" is a non-nucleophile stable group, n is 1 or 2, and R''' is hydrogen, a protecting group or an acid- or reductive-labile linker attached to a resin or protecting group that is removable under non-nucleophilic conditions. The invention also is directed to nucleophile-stable thioester generating resins comprising an orthothioloester or a carboxyester thiol. The nucleophile-stable thioester generating resins have the formulae X—C(OR')$_2$—S—R-linker-resin, X—C((OR$_1$'-linker-resin)(OR$_2$'))—S—R, X—C(O)—O—CH(R")—(CH$_2$)$_n$—S-linker-resin, or X—C(O)—O—CH(R"-linker-resin)-(CH$_2$)$_n$—S—R'''. Also provided are methods for producing the nucleophile-stable thioester generating compounds of the invention, intermediate compositions, and methods of use.

The compounds of the invention are stable to nucleophiles employed in nucleophile-mediated organic synthesis schemes, such as Fmoc-based SPPS, during convergent or compatible selective ligation schemes, and more generally under conditions in which hydroxide ions or other strong nucleophiles are present or generated, and therefore find a wide range of uses. For example, the nucleophile-stable orthothioloester or carboxyester thiol-containing component can be made in the presence of hydroxide ions or other strong nucleophiles, and then converted to the active thioester form when convenient. To activate the nucleophile-stable orthothioloester, the oxygen protecting groups are simply removed from the orthothioloester using a non-nucleophilic reagent such as a strong acid. The resulting thioester-activated component is then ready for use in any of a number of thioester-mediated ligation reactions. The nucleophile-stable carboxyester thiols of the invention are activated by admixing a thiol catalyst. Addition of a thiol catalyst promotes intramolecular thioester formation so as to facilitate thioester-mediated ligation with a component of interest bearing a nucleophilic group.

Accordingly, the nucleophile-stable thioester-generating compounds and methods of the invention greatly expand the utility of nucleophilic synthesis schemes, particularly solid phase or solution phase Fmoc-based small molecule and peptide synthesis schemes. This enables the products of such schemes to be employed, inter alia, in a wide range of thioester-mediated ligation reactions for production of small organic molecules, peptides and polypeptides, other polymers and the like.

For example, as shown in (A) and (B), the synthesized material can be incubated in the presence of a nucleophile or base (e.g., piperidine) under conditions sufficient to cleave the Fmoc group, and subsequently under acid conditions sufficient to permit the conversion of the orthothioloester —C(OR')2S— into the thioester —C(O)S—. As shown in (A), the linker used to tether the polypeptide to the resin can be selected such that it is resistant to acid (HF, TFA, etc.) cleavage under conditions that are sufficient to form the thioester. Thus, in this embodiment, the amino group(s) protected by Fmoc will become deprotected, and a thioester will be formed, but the polypeptide will remain tethered to the solid support. As shown in (B), the linker used to tether the polypeptide to the resin can alternatively be selected such that it is cleaved under the conditions used to form the thioester. Thus, in this embodiment, the amino group(s) protected by Fmoc will become deprotected, a thioester will be formed, and the polypeptide will be released from the solid support.

As shown in (C) and (D), it is alternatively possible to incubate the synthesized material in the presence of a nucleophile or base (e.g., piperidine) under conditions sufficient to cleave the Fmoc group, without incubating the reactants under the acid conditions sufficient to permit the conversion of the orthothioloester —C(OR')$_2$S— into the thioester —C(O)S—. These embodiments permit one to remove the Fmoc groups without creating a thioester. Thus, as shown in (C), one may remove the Fmoc group and, prior to either cleaving the polypeptide or protein from the solid support, or forming the thioester, deprotect residues that are less susceptible than the linker to acid cleavage. Alternatively, as shown in (D), one may remove the Fmoc group and, cleave the polypeptide or protein from the solid support, and deprotect other protected residues prior to forming the thioester.

The methods of the present invention permit one to employ various combinations of such strategies (for example using in the same synthesis, deprotecting groups that are more acid labile than the linker for some residues and other deprotecting groups that are less acid labile than the linker for other residues, etc).

Figure 2:
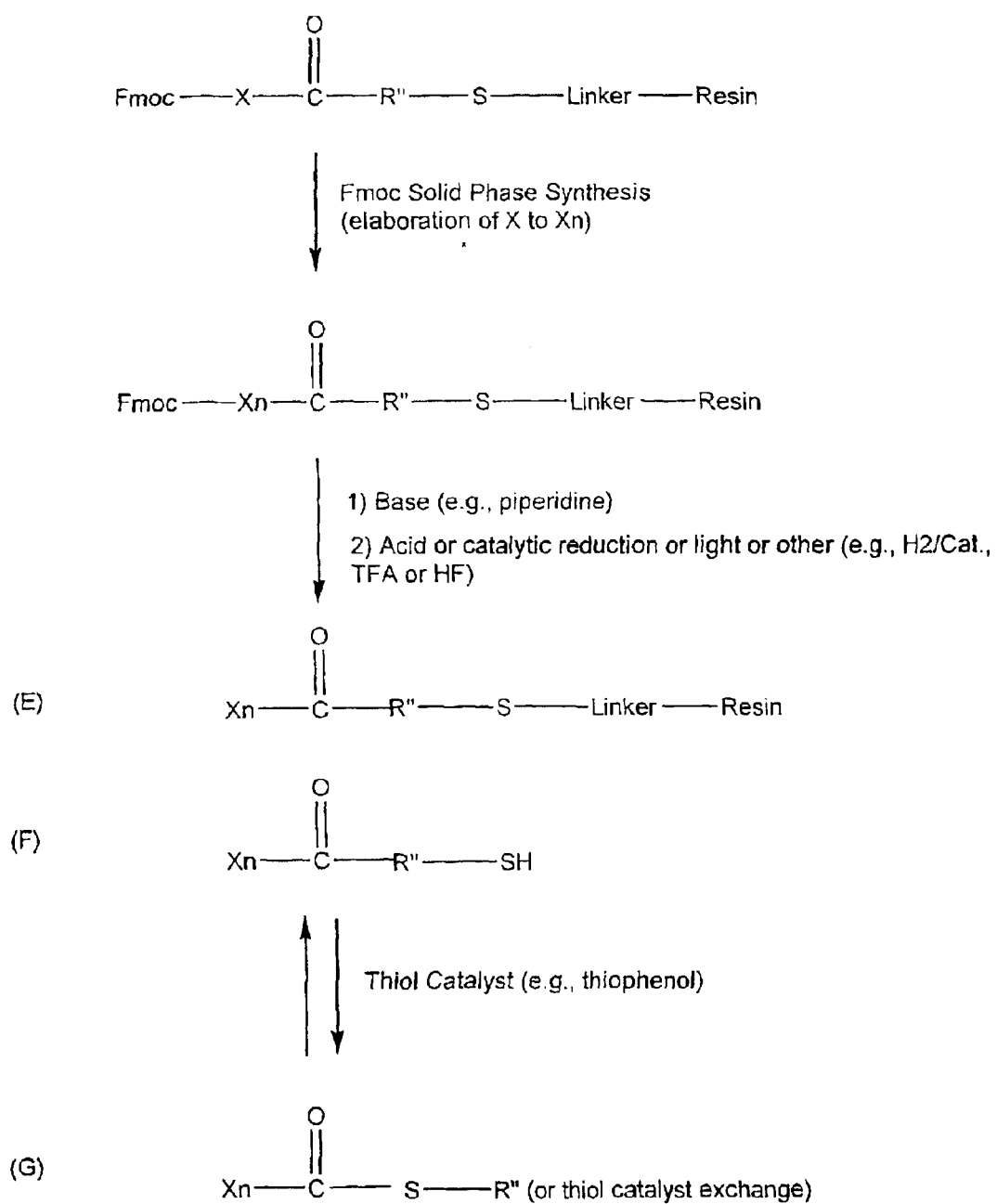

FIG. 2 shows a nucleophile-stable Fmoc-carboxy ester alkylthiol thioester-generating resin and scheme for production of various nucleophile-stable intermediates and an activated-thioester target X—C(O)SR upon activation with a thiol catalyst. The Figure illustrates the substantial flexibility of chemical synthesis that is obtained through the use of such reagents. For example, as shown in (E), linker and residue protecting groups are selected such that the synthesized material can be incubated under conditions sufficient to remove the Fmoc protecting group, and then under conditions sufficient to deprotect residues whose protecting groups are more acid labile than the linker. In this embodiment, the Fmoc-protected residues and acid labile residues are deprotected without either forming the thioester or releasing the synthesized material from the resin. Subsequent cleavage of the linker under suitable conditions can be used to release the compound-carboxyester alkylthiol into solution, where it may be converted to a thiol ester by addition of a catalytic thiol. Alternatively, as shown in (F), linker and residue protecting groups may be selected such that the synthesized material can be incubated under one or more sets of conditions sufficient to remove the Fmoc, and release the synthesized product from the resin, without forming the thioester. In this embodiment, the synthesized material is released from the resin and such selected residue protecting groups that are more labile than the linker are removed, while such selected residue protecting groups that are less acid labile than the linker are retained. In yet another embodiment (G), the thiol catalyst is added such that the carboxy thiol thioester is converted into a thioester. Such addition may be made prior to or after either the addition of base or acid. Thus, after the synthesized product has been Fmoc-deprotected, it may be cleaved from the resin, or have its protected residues deprotected, in any order. Moreover, the methods of the present invention permit one to employ various combinations of such strategies (for example using in the same synthesis, deprotecting groups that are more acid labile than the linker for some residues and other deprotecting groups that are less acid labile than the linker for other residues, etc.

Figure 3:
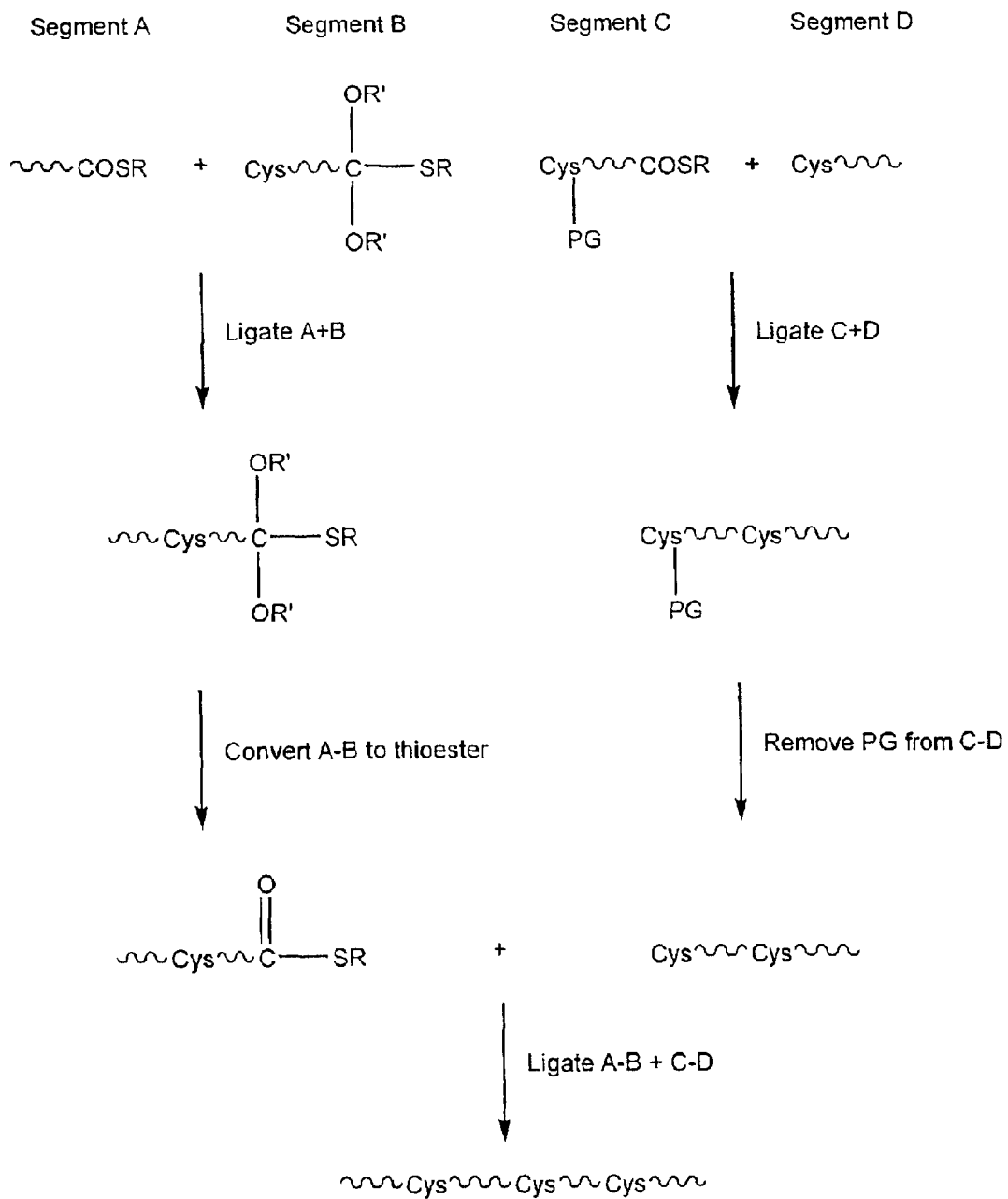

FIG. 3 shows a convergent scheme for synthesis of a target molecule by native chemical ligation, in this example, hypothetical peptide segments A, B, C and D, with a nucleophile-stable Fmoc-generated orthothioloester segment to generate the polypeptide ligation product A-cys-B-cys-C-cys-D, linked through native amide bonds at cysteine ligation sites. The Figure illustrates the power of the methods of the present invention to mediate the bi-directional organic synthesis of proteins, polypeptides and polymers. As shown in the Figure, the method is capable of linking multiple "segments" (which may be derivatized protein, polypeptide, amino acid, resin, nucleic acid, carbohydrate, polymer, etc.). Any number of such segments can be linked. In accordance with the method, the thioester moiety of a "Segment A" thioester is reacted with a cysteine residue of a "Segment B" thioester. The "Segment B" thioester also contains an orthothioloester moiety. The amino nitrogen and sulfur atoms of the cysteine residue attack the "Segment A" thioester carbon, leading to the transient formation of a five membered ring. This ring spontaneously resolves to form a ligated "Segment AB" product in which an amide bond links the carbon of the former thioester and the amino nitrogen atom, and in which the cysteine residue is regenerated. The reaction between "Segment A" and "Segment B" does not involve or affect the orthothioloester moiety of "Segment B." Using the methods of the present invention, the orthothioloester moiety of "Segment B" is converted into a thioester, thereby generating a compound that can, like "Segment A," be further extended. The reactions of "Segment A" and "Segment B" illustrate peptide synthesis in an amino-to-carboxy direction. In the second embodiment shown in FIG. 3, peptide synthesis in a carboxy-to-amino direction is provided. "Segment C" (a derivatized protein, polypeptide, polymer, carbohydrate, nucleic acid or amino acid containing a protected ("PG") cysteine residue and a thioester) is reacted with "Segment D" (cysteine, or an N-terminal cysteine-containing protein, polypeptide, polymer). As in the case of Segments A and B, the reaction resolves to form a ligated "Segment CD" product in which an amide bond links the carbon of the former thioester and the amino nitrogen atom of the former N-terminal Cys of segment D, and in which the cysteine residue side chain thiol is regenerated. Upon removal of the PG protecting group, the ligated molecule, like "Segment D," can be further extended. Significantly, upon formation of its thioester moiety, the Segment AB ligation product can be ligated to the Segment CD ligation product, thereby comprising a convergent synthetic scheme for the production of a Segment ABCD ligation product.

Figure 4:
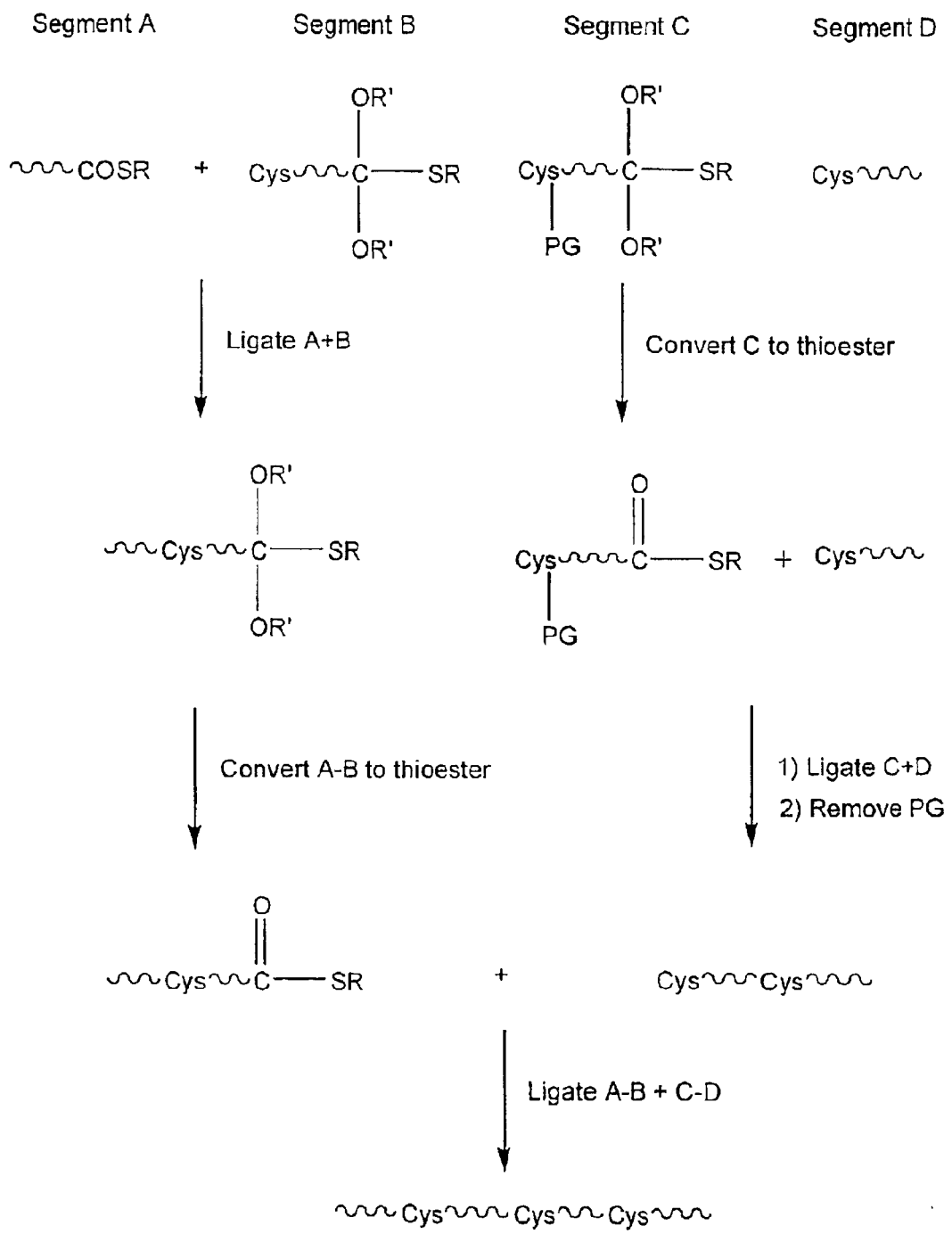

FIG. 4 shows an alternative convergent scheme to that depicted in FIG. 3 for native chemical ligation of target molecule, in this example, hypothetical peptide segments A, B, C and D, with nucleophile-stable Fmoc-generated orthothioloester segments to produce the polypeptide ligation product A-cys-B-cys-C-cys-D, linked through native amide bonds at cysteine ligation sites.

DESCRIPTION OF SPECIFIC EMBODIMENTS OF THE INVENTION

The invention is directed to nucleophile-stable thioester generating compounds comprising an orthothioloester or a carboxyester thiol, methods of production and use. The compounds and methods have wide applicability in organic synthesis, including the generation of peptide-, polypeptide- and other polymer-thioesters. The invention is particularly useful for generating activated-thioesters from precursors that are made under conditions in which strong nucleophiles are employed, such as peptides or polypeptides made using Fmoc SPPS, as well as multi-step ligation or conjugation schemes that require (or benefit from the use of) compatible selective-protection approaches for directing a specific ligation or conjugation reaction of interest.

The nucleophile-stable orthothioloesters of the invention have the formula X—C(OR')$_2$—S—R, where X is a target molecule of interest optionally comprising one or more nucleophile cleavable protecting groups, R' is a nucleophile-stable protecting group that is removable under non-nucleophilic cleavage conditions, and R is any group compatible with the ortholothioester —C(OR')—S—. Nucleophile-stable orthothioloester thioester-generating resins also are provided, and have the formula X—C(OR')$_2$—S—R-linker-resin or X—C((OR$_1$'-linker-resin)(OR$_2$'))—SR, where X, R' and R are as above, and where the linker and resin are any nucleophile-stable linker and resin suitable for use in solid phase organic synthesis, including safety-catch linkers that can be subsequently converted to nucleophile-labile linkers for cleavage.

Examples of the target molecule X include, but are not limited to, any moiety comprising one or more reactive functional groups, such as an amine, protected with a nucleophile-labile protecting group (i.e., a protecting group that is cleavable under nucleophilic conditions), such as an Nα amino group of an amino acid protected with a nucleophile-labile Fmoc group. Accordingly, X may include reactive functional group containing compounds that occur naturally or are made to contain them including amino acids or amino acid derivatives, peptides, polypeptides, nucleic acids, lipids, carbohydrates, water-soluble polymers such as polyalkylene oxide, polyamides, copolymers thereof and the like, provided that at least one reactive functional group thereon comprises a nucleophile-labile protecting group. Many such protecting groups are known and suitable for this purpose (See, e.g., "Protecting Groups in Organic Synthesis", 3rd Edition, T. W. Greene and P. G. M. Wuts, Eds., John Wiley & Sons, Inc., 1999; NovaBiochem Catalog 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; and "Protecting Groups," P. J. Kocienski, Ed., Georg Thieme Verlag, Stuttgart, Germany, 1994).

Examples of R include, but are not limited to, aryl, benzyl, and alkyl groups. Preferred embodiments include 3-carboxy-4-nitrophenyl thioesters, benzyl thioesters, mercaptoacetic acid thioesters and mercaptoproprionic acid leucine esters (See, e.g., Dawson et al., Science (1994) 266:776–779; Canne et al. Tetrahedron Lett. (1995) 36:1217–1220; Kent, et al., WO 96/34878; Kent, et al., WO 98/28434; Ingenito et al., JACS (1999) 121(49): 11369–11374; and Hackeng et al., Proc. Natl. Acad. Sci. U.S.A. (1999) 96:10068–10073).

Examples of R' include, but are not limited to, protecting groups that are stable to nucleophiles (i.e., nucleophile-stable protecting groups) but labile under acidic conditions (i.e., non-nucleophile labile protecting groups), such as hydrogen generators with catalyst ("H2/Cat." or other reducing agents), or strong acids like trifluoroacetic acid ("TFA") or hydrogen fluoride ("HF"). This includes any protecting group compatible with Fmoc SPPS, provided that the protecting group R' is nucleophile-stable and non-nucleophile-labile. Many such protecting groups are known and suitable for this purpose (See, e.g., "Protecting Groups in Organic Synthesis", 3rd Edition, T. W. Greene and P. G. M. Wuts, Eds., John Wiley & Sons, Inc., 1999; NovaBiochem Catalog 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; and "Protecting Groups," P. J. Kocienski, Ed., Georg Thieme Verlag, Stuttgart, Germany, 1994).

The R' group can be an independent protecting group that is conjugated to an independent oxy group on the orthothioloester —C[(OR$_1$')(OR$_2$')], which when referred to specifically is termed herein a "non-cyclic orthothioloester protecting group". Alternatively, the R' group can form a dioxycyclic structure that connects and protects both oxy groups —C(O—R'—O), which when referred to specifically is termed herein a "cyclic orthothioloester protecting group". These compounds are illustrated below, where the compound on the left comprises a cyclic orthothioloester, and the compound on the right comprises a non-cyclic orthothioloester.

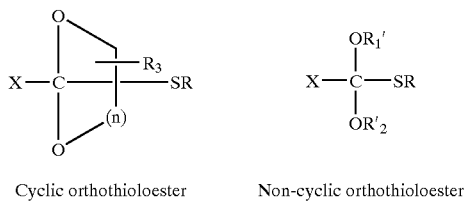

Cyclic orthothioloester      Non-cyclic orthothioloester

For the cyclic orthothioloester: (n)=1 to 7 carbons; and R3 is present or absent and may be present individually, or as two or more identical or mixed substituents on the dioxycyclic backbone, and is a moiety for tuning the lability of R' to non-nucleophiles. $R_3$ preferably comprises an electron-withdrawing or donating group that increases stability to non-nucleophilic protecting group R' removal. Cyclic orthothioloesters where (n)=1 to 5, and more preferably (n)=1 to 3, with (n)=1 to 2 most preferred, and where R3 is an alkyl, benzyl, or aryl group are preferred. The R3 alkyl, benzyl, or aryl groups can be or comprise linear, branched, substituted or non-substituted cyclic aromatic or non-aromatic, heterocyclic aromatic or non-aromatic structure, which are chosen to tune the properties of a given cyclic orthothioloester depending on its intended end use. In general, the R3 alkyl, benzyl and aryl groups are those employed in SPPS, and are compatible with acidic or reductive cleavage. Suitable electron withdrawing groups include but are not limited to heteroatom(s) in different oxidation states (except for O⁻), carbonyl, nitrile, sulfoxy, sulfone, sulfate, and halogen groups. Suitable electron donating groups include but are not limited to aliphatic, branched aliphatic, benzyl, substituted benzyl groups. Preferred electron withdrawing groups include ketone, ester, amide, I, Br, Cl, F, nitrile, sulfoxy, sulfone, and benzyl group substituted with one or more electron withdrawing groups. Preferred electron donating groups include —CH3, —CH2-CH3, —CH2(CH3)2, —CH2-CH2(CH3)2, and benzyl group substituted with one or more electron donating groups. In a preferred embodiment, R3 comprises an electron-withdrawing group that is stable to nucleophilic cleavage conditions (i.e., nucleophile stable). Various electron donating and withdrawing groups suitable for use herein, such as those described above, are disclosed at page 18, in "Advanced Organic Chemistry, Reactions, Mechanisms, and Structure," 4th Edition, J. March (Ed.), John Wiley & Sons, New York, N.Y., 1992. It will be appreciated that R3 can include spacer groups, typically —CH$_2$— groups, which can be selected so as to tune the stability of the R' protecting group to non-nucleophilic cleavage or to ease or improve synthesis for a particular target molecule, and may be provided in reduced or non-reduced forms.

Referring to the non-cyclic orthothioloesters, where R' is an independent oxy protecting group R1' and R2', the R1' and R2' groups may be the same or different, and are selected from an alkyl, benzyl, or aryl group. The preferred R1' and R2' alkyl, benzyl, or aryl groups comprise an electron-withdrawing or electron-donating group, and are preferably the same. The R1' and R2' groups can comprise linear, branched, substituted or non-substituted cyclic aromatic or non-aromatic, heterocyclic aromatic or non-aromatic structure, which are chosen to tune the properties of a given non-cyclic orthothioloester depending on its intended end use. In general, the R1' and R2' groups are those employed in SPPS, and are compatible with acidic or reductive cleavage. In a preferred embodiment, R1' and R2' comprise electron-withdrawing groups that are stable to nucleophilic cleavage conditions (i.e., nucleophile stable). Suitable electron withdrawing groups include but are not limited to heteroatom(s) in different oxidation states (except for O⁻), carbonyl, nitrile, sulfoxy, sulfone, sulfate, and halogen groups. Suitable electron donating groups include but are not limited to aliphatic, branched aliphatic, benzyl, substituted benzyl groups. Preferred electron withdrawing groups include ketone, ester, amide, I, Br, Cl, F, nitrile, sulfoxy, sulfone, and benzyl group substituted with one or more electron withdrawing groups. Preferred electron donating groups include —CH3, —CH2—CH3, —CH2(CH3)2, —CH2-CH2(CH3)2, and benzyl group substituted with one or more electron donating groups. Various electron donating and withdrawing groups suitable for use herein, such as those described above, are disclosed at page 18, in "Advanced Organic Chemistry, Reactions, Mechanisms, and Structure," 4th Edition, J. March (Ed.), John Wiley & Sons, New York, N.Y., 1992. It will be appreciated that R3 can include spacer groups, typically —CH2— groups, which can be selected so as to tune stability of the R' protecting group to non-nucleophilic cleavage or to ease or improve synthesis for a particular target molecule, and may be provided in reduced or non-reduced forms.

The nucleophile-stable orthothioloesters of the invention may be synthesized in solution, by polymer-supported synthesis, or a combination thereof as described herein and in accordance with standard organic chemistry techniques known in the art. See, e.g., "Advanced Organic Chemistry, Reactions, Mechanisms, and Structure," 4th Edition, J. March (Ed.), John Wiley & Sons, New York, N.Y., 1992; "Comprehensive Organic Transformations, A Guide to Functional Group Preparations," R. Larock (Ed.), VCH Publishers, New York, N.Y., 1989; "Protecting Groups in Organic Synthesis", 3rd Edition, T. W. Greene and P. G. M. Wuts, Eds., John Wiley & Sons, Inc., 1999; Feugeas et al., C.R. Acad. Sci., Paris, Ser.C (1968) 266(20):1506–1507; and Honma et al., Chem. Pharm. Bull. (1976) 24(4): 818–820). Solution and solid phase approaches for synthesizing orthothioloester thioester-generating resins of the invention are exemplified in Schemes I to III below for Fmoc-amino acids. In Schemes I to III, Rs is an amino acid side chain of interest, which can be a genetically encoded or non-coded amino acid side chain or derivative thereof and may be protected or unprotected, and Z is a protecting group that may be present or absent, and can be a variety of groups depending on a given synthesis scheme, such as Fmoc, benzyloxycarbonyl (Z- or Cbz-) or tert-butyloxycarbonyl ("Boc") groups. The reagents utilized for synthesis can be obtained from any number of commercial sources, or prepared de novo. Also, it will be understood that the starting components and various intermediates, such as an orthothioloester thioester-generating compound having a first amino acid or other compound X for subsequent elaboration in an organic synthesis scheme of interest can be stored for later use, provided in kits and the like.

In general, the orthothioloesters are made by converting precursor orthoesters to an orthothioloester in a thiol exchange reaction. More particularly, an orthoester X—C(OR')3 is prepared as a precursor that comprises a desired nucleophile-stable protecting group of interest following standard protocols (See, e.g., In "Protecting Groups in Organic Synthesis", 3rd Edition, T. W. Greene and P. G. M. Wuts, Eds., John Wiley & Sons, Inc., pp. 437 ff, 1999; McElvin et al., J. Amer. Chem. Soc. (1942) 64:1825; R. H. Dewolf, Synthesis (1974) 153; Feugeas et al., C.R. Acad. Sci., Paris, Ser.C (1968) 266(20):1506–1507; and Honma et al., Chem. Pharm. Bull. (1976) 24(4):818–820). In a preferred embodiment, the orthoester precursors are constructed from nitriles involving a final Lewis Acid catalyzed transorthoesterfication reaction, which is depicted in Scheme I below. In this approach, the nitrile form of target molecule X is admixed with a strong acid such as HCl or HBr and an excess of a priming alcohol, such as methanol or ethanol, or the alcohol form of the protecting group R', i.e., R'OH. The primary alcohol-modified nitrile is then converted to the desired orthoester precursor X—C(OR')3 by reaction with the alcohol form of the protecting group of interest R'OH in the presence of a suitable Lewis Acid, such as AlCl3, BF3·Et2O or SnCl4. Alternatively, the nitrile can be converted to an iminoester with a first alcohol R'OH, followed by its conversion to the desired precursor orthoester X—C(OR')3 by addition of a second R'OH in the presence of a Lewis Acid catalyst; in most instances the first and second alcohol's R'OH are the same, but may be different if a mixed orthoester is desired; for instance, the first alcohol can be a priming alcohol if a mixed construct is desired. To generate the cyclic orthothioloester precursor, the dialcohol form of the protecting group of interest, namely OH—R'—OH is admixed with either the primary alcohol-modified orthoester or with an orthoester derived from the iminoester, with a Lewis Acid being the catalyst. To generate the non-cyclic version, a monoalcohol is employed. Orthoester precursors also may be prepared from the acids, but this route is less preferred. In some instances a non-Lewis Acid 1,1,1-trihalide can be used as the catalyst, but this also is less preferred.

Pharm. Bull. (1976) 24(4):818–820). This is illustrated for Fmoc-amino acid orthothioloesters below in Schemes II and III.

Scheme II

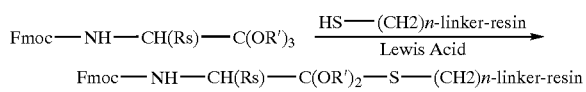

Scheme III

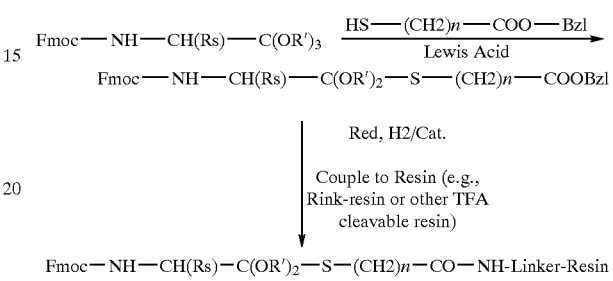

Figure 1:
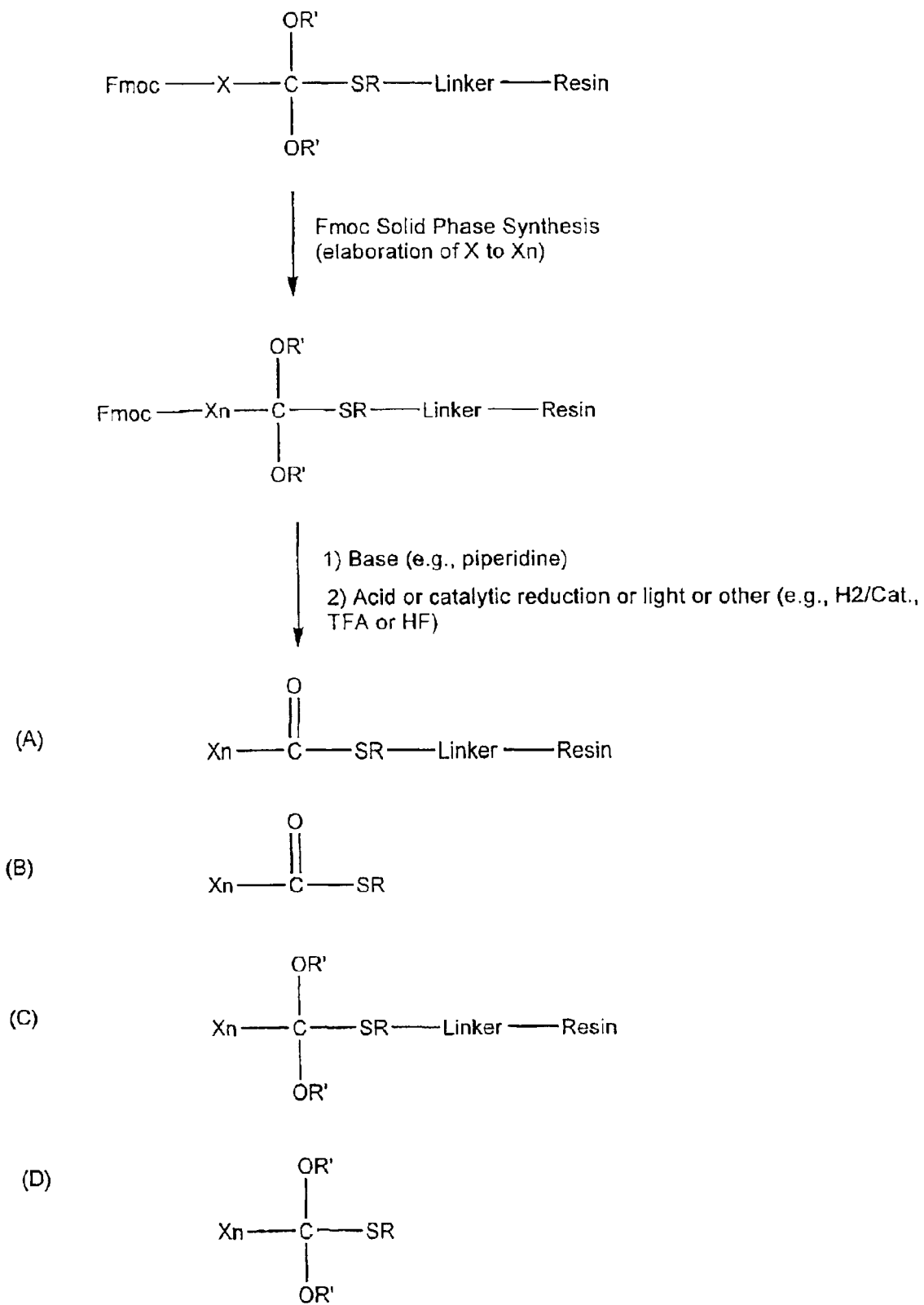
FIG. 1 shows a nucleophile-stable Fmoc-orthothioloester thioester-generating resin and a reaction scheme for producing various nucleophile-stable intermediates and a target activated-thioester X—C(O)SR. The Figure illustrates the substantial flexibility of compatible selective protection approaches to chemical synthesis permitted through the use of such reagents. The invention permits one to select tethering linkers and residue protecting groups that are either the same or different with respect to their acid lability. Likewise, the addition of acid (for cleaving the linker and/or forming the thioester) may be accomplished either before or after the addition of base (for removing the Fmoc moiety). Thus, through selection of appropriate acid-labile protecting groups such as Benzyl, Trt, etc., the invention permits one to synthesize products that can be deprotected while still bound to the resin (i.e. the residue protecting groups are selected such that they are more acid labile than the linker). Alternatively, one may synthesize products that can be released from the resin and then deprotected (i.e. the residue protecting groups are selected such that they are less acid labile than the linker). Myriad synthetic variations are thus provided.

As illustrated in FIGS. 1 and 2, the orthothioloester may be incorporated on-resin in an Fmoc-compatible synthesis of a target molecule X. The linker and resin system is chosen depending on a given end use; many such systems are well known and suitable for this purpose (See, e.g., The Combinatorial Index, B. A. Bunin, Acedemic Press, 1998; NovaBiochem Catalog 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R.

Scheme I

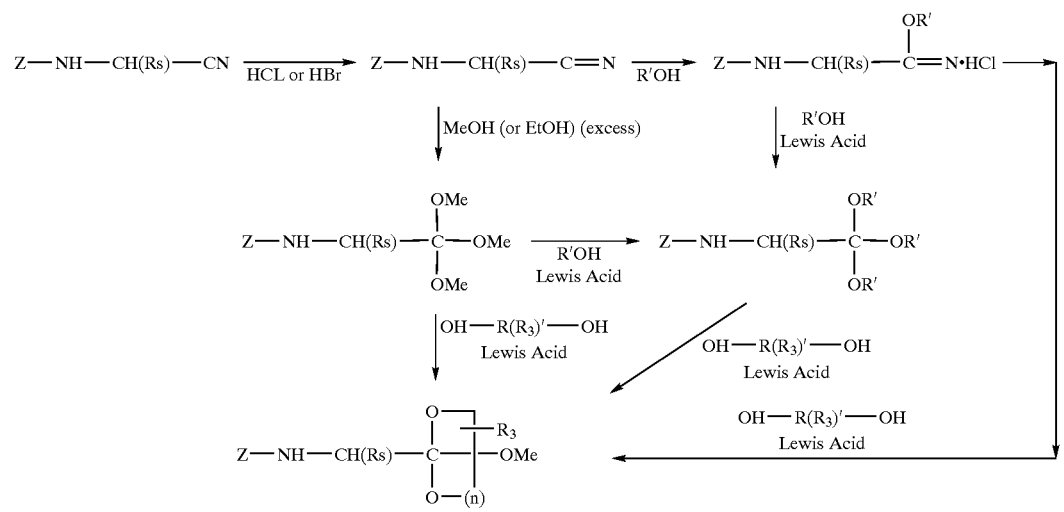

Once the orthoester precursor X—C(OR')3 is made, it can be stored for later use or immediately converted to the desired orthothioloester X—C(OR')2-S— by an exchange reaction in the presence of a Lewis acid, such as AlCl3, with an alkyl, benzyl or aryl thiol of interest following standard procedures (Feugeas et al., C.R. Acad. Sci., Paris, Ser.C (1968) 266(20):1506–1507; and Honma et al., Chem.

Rhodes, and H. H. Saneii, Eds., Advanced Chemtech, 1998; "Principles of Peptide Synthesis, 2nd ed.," M. Bodanszky, Ed., Springer-Verlag, 1993; and "The Practice of Peptide Synthesis, 2nd ed.," M. Bodanszky and A. Bodanszky, Eds., Springer-Verlag, 1994).

Selection of protecting group R' in combination with the linker and resin system provide for additional flexibility. For example, depending on protecting group R', and the linker attaching the orthothioloester to the resin, any number of compatible selective or non-selective on-resin synthesis, cleavage and thioester activation strategies can be exploited. Compatible selective protection schemes involve two or more classes or groups that are removed by differing chemical mechanisms, and therefore can be removed in any order and in the presence of the other classes. Compatible selective schemes offer the possibility of substantially milder overall conditions, because selectivity can be attained on the basis of differences in chemistry rather than reaction rates. For instance, when Fmoc chemistry is employed for peptide synthesis, i.e., where X is an Fmoc protected amino acid or peptide, although piperidine is used in each cycle of amino acid addition, the orthothioloester is stable. Once the last coupling cycle of interest is completed, Fmoc groups can be removed using a piperidine cocktail, which is then typically followed by treatment of the peptide resin with a strong acid such as TFA to remove any other TFA-labile side-chain protecting groups that are present. When a TFA labile ortho oxy protecting group R' is employed in the orthothioloester, TFA treatment generates a nucleophile-labile peptide-thioester. Thus, when a synthesis resin comprising a TFA labile linker is employed, such as a Rink linker, then the peptide-thioester is simultaneously generated and cleaved from the resin and an activated peptide-thioester is released in solution. This cleavage product is now suitable for a subsequent thioester-mediated reaction of interest. Alternatively, when an HF labile ortho oxy protecting group system is employed, and a synthesis resin comprising a TFA labile linker is employed, then the TFA treatment generates a nucleophile-stabile peptide orthothioloester in solution. This is particularly useful for production of a peptide bearing an N-terminal reactive group such as cysteine in combination with a C-terminal nucleophile-stable orthothioloester (See, e.g., FIG. 3). If an acid stable linker is employed, then the thioester peptide remains bound to the resin; such may be the case if an enzyme or safety-catch cleavable linker is used. Compatible selective protection may also be applied to the elaborated target molecule X, which can be useful for synthesis of certain constructs as well as in the preparation of intermediates employed in convergent conjugation or ligation schemes (See, e.g., FIGS. 3 and 4). A non-selective approach, where the orthothioloester or carboxyester thiol, linker and non-nucleophile-labile protecting groups on the elaborated target molecule X are labile to the same set(s) of conditions and are cleaved simultaneously can be advantageous for certain targets, and can reduce the number of chemical steps. As is readily apparent, the same fundamental design approach described above for peptides can be applied to other target molecules of interest, such as other polymers and small molecules, and can be used to generate partially protected or fully unprotected target molecules X on resin or in solution.

The nucleophile-stable carboxyester thiols of the invention have the formula X—C(O)—O—CH(R")—(CH$_2$)$_n$—S—R'", where X is a target molecule of interest comprising one or more nucleophile-labile protecting groups, R" is a non-nucleophile stable group, n is 1 or 2, with n=1 preferred, and R'" is hydrogen, a protecting group or an acid- or reduction-labile or safety catch linker attached to a is resin or protecting group that is removable under non-nucleophilic conditions. Nucleophile-stable carboxyester thiol-based thioester-generating resins also are provided, and have the formula X—C(O)—O—CH(R")—CH2n-S-linker-resin or X—C(O)—O—CH(R"-linker-resin)-CH2n-S—R'", where X, R", n and R'" are as above, and where the linker and resin are any nucleophile-stable linker and resin suitable for use in solid phase organic synthesis.

Examples of the target molecule X include, but are not limited to, any moiety comprising one or more reactive functional groups, such as an amine, protected with a nucleophile-labile protecting group (i.e., a protecting group that is cleavable under nucleophilic conditions), such as an Nα amino group of an amino acid protected with a nucleophile-labile Fmoc group. Accordingly, X may include reactive functional group-containing compounds that occur naturally or are made to contain them including amino acids or amino acid derivatives, peptides, polypeptides, nucleic acids, lipids, carbohydrates, water-soluble polymers such as polyalkylene oxide, polyamides, copolymers thereof and the like, provided that at least one reactive functional group thereon comprises a nucleophile-labile protecting group. Many such protecting groups are known and suitable for this purpose (See, e.g., "Protecting Groups in Organic Synthesis", 3rd Edition, T. W. Greene and P. G. M. Wuts, Eds., John Wiley & Sons, Inc., 1999; NovaBiochem Catalog 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; and "Protecting Groups," P. J. Kocienski, Ed., Georg Thieme Verlag, Stuttgart, Germany, 1994).

The R" group can be any of a variety of different electron withdrawing or donating groups that are selected to have the following properties: i) render the ester stable to acidic or reductive cleavage conditions (i.e., non-nucleophile stable); and ii) permits thioesterfication exchange reaction in the presence of a catalytic thiol. Suitable R" groups can be selected from aliphatic, branched aliphatic, heteroatom, carbonyl, benzyl, nitrile, sulfoxy, sulfone, sulfate, and halogen groups. Preferred embodiments include —CH$_3$, —CH$_2$—CH$_3$, —CH$_2$(CH$_3$)$_2$, —CH$_2$—CH$_2$(CH$_3$)$_2$, methoxy, ketone, ester, amide, Br, Cl, F, nitrile, sulfoxy, sulfone, and benzyl group substituted with one or more electron withdrawing or donating groups. The thiol catalyst can be unconjugated mercaptan or a conjugated thiol. Preferred catalytic thiols include benzyl mercaptan, thiophenol, 1-thio-2-nitrophenol, 2-thio-benzoic acid, 2-thio-pyridine, 4-thio-2-pyridencarboxylic acid, and 4-thio-2-nitrophenol, with thiophenol being the most preferred.

Any number of approaches can be employed for making the nucleophile-stable carboxyester thiols of the invention, as described herein, for example, in Scheme VII through Scheme IX, the Examples, and in accordance with standard organic chemistry techniques known in the art. See, e.g., "Advanced Organic Chemistry, Reactions, Mechanisms, and Structure," 4th Edition, J. March (Ed.), John Wiley & Sons, New York, N.Y., 1992; "Comprehensive Organic Transformations, A Guide to Functional Group Preparations," R. Larock (Ed.), VCH Publishers, New York, N.Y., 1989; and "Protecting Groups in Organic Synthesis", 3rd Edition, T. W. Greene and P. G. M. Wuts, Eds., John Wiley & Sons, Inc., 1999). The preferred approach employs a thioalcohol precursor of the formula PG-S—CH2n-CH(R")OH or a thioketone of the formula PG-S—CH2n-CO(R"), where PG is an nucleophile-stable protecting group. Solid phase synthesis using the thioalcohol and base-catalyzed carboxyesterification (e.g., a base catalyst such as dimethylaminopyridine "DMAP") is exemplified in Schemes IV to VI below, which illustrate the generation of Fmoc-amino acid carboxyester thiols. In Scheme IV, coupling through the thiol to a linker is shown, where R''' is free. Scheme V illustrates coupling through R'' as shown. The same basic synthesis scheme can be employed for non-amino acids. Also, for the thioketone precursor, the ketone is converted to the thioalcohol form followed by carboxyesterification. The linker employed is preferably acid labile, such as a TFA-cleavable linker-resin system, such as a Wang resin.

Scheme IV

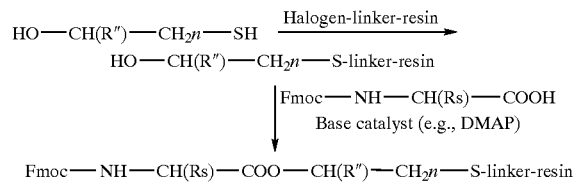

Scheme V

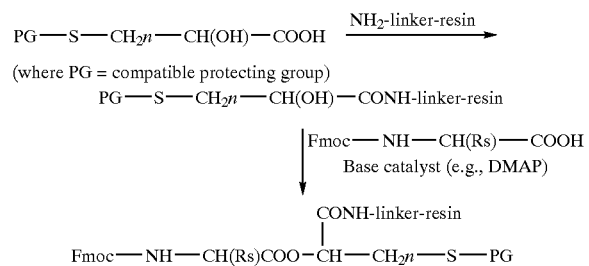

Scheme VI

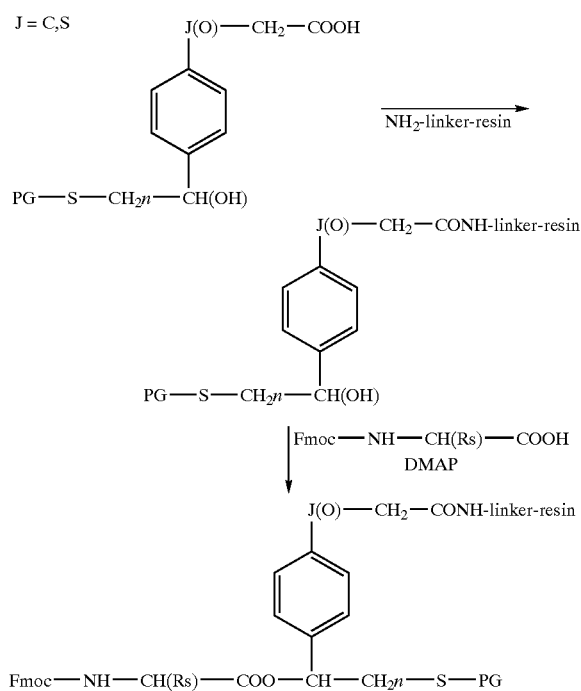

The nucleophile-stable thioester-generating orthothioloesters and carboxyester thiols of the invention find particular use in the synthesis of thioesters employed in conjugation and ligation reactions. For instance, they may be applied to the thioester-mediated chemoselective ligation of peptides and polypeptides, such as native chemical ligation (Dawson, et al., Science (1994) 266:776–779; Kent, et al., WO 96/34878; Kent, et al., WO 98/28434). A peptide containing a C-terminal or side chain thioester can be made using an orthothioloester and carboxyester thiol composition of the invention in conjunction with Fmoc synthesis. A peptide or polypeptide comprising an N-terminal Cys residue can be made using Fmoc or Boc chemistry, or by biological means such as recombinant DNA expression, or combinations thereof, depending on the intended end use.

The methods and copositions of the present invention thus provide the advantage of permitting the use of nucleophile-sensitive (for example, Fmoc, etc.) protecting strategies, in addition to nucleophile-insensitive strategies (such as Boc protection strategies). Such chemistry permits the attachment of acid-labile groups such as steroids, fluorescein, and folic acid to the synthetic protein or polypeptide. Additionally, the present invention permits the use of conventional Fmoc reagents as well as modified Fmoc reagents in chemical ligation reactions. In particular, the present invention permits one to form Fmoc MAP (Multiple Antigenic Peptide) derivatives of any desired synthetic peptide or polypeptide. Fmoc MAP reagents typically have multiple (e.g., 4 or 8) peptide arms branching out from a lysine core matrix. Their use is thought to increase the antigenicity of a peotide. MAP-peptides used in experimental vaccine design have elicited high titers of anti-peptide antibodies that recognize the native protein (Tam, J. P., (1988) Proc. Natl. Acad. Sci. U.S.A. 85, 5409–5413; Posnett, D. N. et al. (1988) J. Biol. Chem. 263, 1719–1725; Auriault, C. et al. (1991) Peptide Res. 4, 6–11. An anti-V3 loop AIDS vaccine has been reported to stimulate higher levels of antibodies, compared with other vaccines, and to induce more persistent immune responses (Wang, C. Y. et al. (1991) Science, 254, 285–288). Additionally, increased sensitivity and reliability of antibody-antigen interactions in solid-phase immunoassays have been observed with MAP-peptides due to enhanced coating capacity and avidity (Tam, J. P., and Zavala, F., (1989) J. Immunol. Meth. 124, 53–61). The MAP approach removes the need to conjugate peptides to carrier proteins that may alter the antigenic determinants.

The methods of the present invention facilitate the compatible selective protection of reactive groups, and thus permit convergent synthetic schemes for the ligation of multiple (peptide) segments to be conducted, thereby increasing theoretical maximal yields of product.

The ability of the present invention to provide enhanced compatible selective protection permits one to conduct multiple reactions in a single vessel, or in fewer reaction vessels than would otherwise be required.

Additionally, the capacity to synthesize peptides and polypeptides using Fmoc chemistry facilitates the use of peptide inversion technologies to invert the synthesized peptides thus permitting modifications to be introduced into the C-terminus of the peptide (see, e.g., M. Davies et al. (1998) J. Org. Chem. 8696–8703; M. Davies et al., (1997) Angew. Chem. 109:1135–1138):

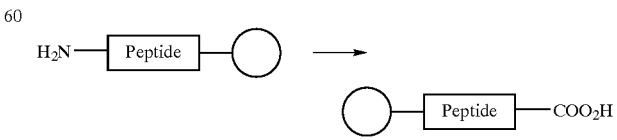

All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless specified.

EXAMPLES

The following preparations and examples are given to enable those skilled in the art to more clearly understand and to practice the present invention. They should not be considered as limiting the scope of the invention, but merely as being illustrative and representative thereof.

Example 1

Preparation of Chloro-Wang resin (p-benzyloxybenzyl chloride resin)

A Chloro-Wang resin (p-benzyloxybenzyl chloride resin) was prepared by dissolving N-Chlorosuccinimide (5 mmol, 667 mg) in 10 ml of THF. Triphenylphosphine (5 mmol 1.31 g) was dissolved in 10 ml of THF and added to the N-chlorosuccinimide solution. A white solid precipitated, to which an additional 10 ml of THF was added and after 5 minutes. 1 g of Wang resin (0.7 mmol/g) was then added to the mixture, and the reaction allowed to proceed overnight. The Chloro-Wang-resin was then washed several times with DMF and DCM, and dried under vacuum.

Example 2

Preparation of p-benzyloxybenzylthioethanol resin

A p-benzyloxybenzylthioethanol resin for coupling Fmoc-protected amino acids was prepared as follows. A mixture of 1.5 ml of 2-mercaptoethanol, 3 ml of DIEA and 8 ml of DMF was added to 350 mg of Chloro-Wang resin as prepared in Example 1. A 2.5 ml flow wash was used and the reaction was allowed to proceed overnight. The resin was then washed several times with DMF and DCM, and dried under vacuum.

Example 3

Preparation of p-benzyloxybenzylthio-2propanol resin

A p-benzyloxybenzylthio-2propanol resin for coupling Fmoc-protected amino acids was prepared as follows. To 350 mg of Chloro-Wang resin prepared as in Example 1, a mixture of 1.5 ml of 1-mercapto-2propanol, 3 ml of DIEA and 8 ml of DMF was added. A 2.5 ml flow wash was used and the reaction allowed to proceed overnight. The resin was then washed several times with DMF and DCM, and dried under vacuum.

Example 4

Coupling of Fmoc-Glycine to p-benzyloxybenzylthio-2propanol resin

A p-benzyloxybenzylthio-2-propyl-FmocGlycine ester resin was prepared as follows. A mixture of 830 mg (2.8 millimole) of Fmoc-Glycine, 0.22 ml (1.4 millimole) of DIC, 17.2 mg (0.14 millimole) of DMAP and 22 mg (0.16 millimole) of HOBT in 3 ml of DMF was preactivated for 30 minutes and then added to the p-benzyloxybenzylthio-2propanol resin. The reaction was allowed to proceed overnight.

Example 5

Fmoc SPPS of peptide on p-benzyloxybenzylthio-2-propyl-Fmoc-Glycine ester resin

A peptide of the sequence FKLAG was synthesized on the Fmoc-Glycine p-benzyloxybenzylthio-2propanol resin following standard Fmoc SPPS procedures. In particular, Fmoc deprotection was accomplished using 20% Piperidine in DMF (2 times for 3 minutes each, per cycle of amino acid addition). Chain assembly was performed using standard HBTU/DIEA activation. In this way a p-benzyloxybenzylthio-2-propyl-peptide ester resin was constructed.

Example 6

Acid cleavage of p-benzyloxybenzylthio-2-propyl-peptide ester resin

A peptide-carboxyester thiol was generated by acid cleavage of the resin-linked peptide of Example 5. The p-benzyloxybenzylthio-2-propyl-peptide ester resin from Example 5 (350 mg) was treated with 5 ml TFA, 0.2 ml water and 0.25 ml thioanisole for 2 hrs. The cleavage product comprising the FKLAG-carboxyester thiol, a 1-mercapto, 2-propylpeptide ester, was purified by HPLC and analyzed by Mass Spec. The purified cleavage product exhibited the expected mass of 609.7 Daltons.

Example 7

Thioester-mediated ligation of 1-mercapto, 2-propylpeptide carboxyester to an N-terminal cysteine-peptide The ability of a peptide-carboxyester thiol to be converted to an activated thioester peptide in the presence of a thiol catalyst was examined by testing the peptide's ability to ligate to a N-terminal cysteine containing peptide. Approximately 0.3 mg of the 1-mercapto, 2-propylpeptide ester of Example 6 (FKLAG-carboxyester isopropyl thiol) and 0.6 mg of N-terminal cysteine peptide (CARHTVHQRHLFG), MW 1562, were admixed with 0.25 ml of 6Molar Guanidinium Buffer pH 7 and 0.02 ml of thiophenol at room temperature. An additional 0.02 ml of thiophenol was added and the reaction allowed to proceed. After four days the major peak revealed by HPLC was analyzed by Mass Spec, which corresponded to a mass of 2078 Da (expected 2079 Da) for the desired ligation product.

Example 8

Preparation of Fmoc-Glycine Orthotrimethylester

Aminoacetonitrile HCL salt (1 mmol (92.53 mg)) is dissolved in DMF 2 ml and DIEA 2 mmol 0.35 ml. Then Fmoc-Succinimidyl dicarbonate 1.1 mmol, (350 mg) is added and the reaction allowed to proceed overnight. Water and diluted HCL is added to bring the pH to 2. The product is extracted 3 times with ethylacetate and dried over $Na_2SO_4$ to yield Fmoc-NH—$CH_2$—CN. 1 mmol of the Fmoc-NH—$CH_2$—CN (278 mg) is dissolved in 2 ml of anhydrous methanol bubbled with HCl gas. The reaction is kept at 0° C. for 40 hrs (Voss and Gerlach Helv. Chim. Acta (1983) 66: 2294) to yield the desired Fmoc-glycine orthotrimethylester (Fmoc-NH—$CH_2$—$C(OCH_3)_3$).

Example 9

On-resin Preparation of Fmoc-Glycine Orthodimethylthioloester Resin

On-resin preparation of a Fmoc-Glycine orthodimethylthioloester thioester-generating resin is conducted as follows. 3,3'-dithiodipropionic acid di(N-hydroxysuccinimidyl ester) (10 mmol (4.04 g)) is coupled to a $NH_2$-{Rink linker}-resin (1 mmol) in 5 ml of DMF. Coupling is monitored by ninhydrin test. The resin is washed with DMF, and a mixture of 10% Piperidine and 10% beta-mercaptoethanol in DMF is added to the resin, with a 1 ml flow wash and 5 ml batch treatment for 30 minutes. The resin is washed with DMF and reacted with 10 mmol of Fmoc-NH—$CH_2$—C($OCH_3$)$_3$ (3.56 g) from Example 8 in presence of 1 mmol $AlCl_3$ (133 mg) in 12 ml of DCM to achieve thiol exchange (Feugeas et al., Lab. Syn. Org. B., Fac. Sci. Marseilles, Fr. C.R. Acad. Sci., Paris Ser. C. (1968) 266(20):1506–1507) to give Fmoc-Glycine orthodimethylthioloester-resin.

Example 10

Solution Phase Preparation of Fmoc-Glycine Orthodimethylthioloester Acid

Bzl-protected Fmoc-Glycine orthodimethylthioloester is prepared in solution as follows. Fmoc-NH—$CH_2$—C($OCH_3$)$_3$ (1 mmol (356 mg)) is reacted with HS—$CH_2$—$CH_2$—$CH_2$—COO-Bzl ester 1 mmol 196 mg in presence of $AlCl_3$ 0.1 mmol (133 mg) and 2 ml of DCM to achieve thiol exchange (Feugeas et al., Lab. Syn. Org. B., Fac. Sci. Marseilles, Fr. C.R. Acad. Sci., Paris Ser. C. 1968, 266(20): 1506–1507), which yields the Bzl-protected Fmoc-Glycine orthodimethylthioloester (Fmoc-NH—$CH_2$—C($OCH_3$)2-S—$CH_2$—$CH_2$—$CH_2$—COO-Bzl) in solution.

To remove the benzyl protecting group, reductive cleavage by H2/Pt is employed ("Protecting Groups in Organic Synthesis," 3$^{rd}$ Edition, T. W. Green and P. G. M. Wuts, Eds., John Wiley & Sons, New York, N.Y., 1992, pp 250–252; and "Protecting Groups," P. J. Kocienski, Ed., Georg Thieme Verlag, Stuttgart, Germany, 1994, pg. 137). 1 mmol of the Bzl-protected Fmoc-NH—$CH_2$—C($OCH_3$)$_2$—S—$CH_2$—$CH_2$—$CH_2$—COO-Bzl is dissolved in anhydrous methanol 10 ml and treated at room temperature for 3 hrs with $H_2$ over 100 mg of Pt catalyst to yield the product Fmoc-NH—$CH_2$—C($OCH_3$)$_2$—S—$CH_2$—$CH_2$—$CH_2$—COOH. The Fmoc-Glycine orthodimethylthioloester acid can be utilized for solution phase coupling, or attached to a $NH_2$-Rink resin using standard HBTU/DIEA coupling protocol to give Fmoc-Glycine orthodimethylthioloester-resin.

Example 11

Preparation of Fmoc-Glycine Cyclic Orthoethylesters

Fmoc-NH—$CH_2$—CN (1 mmol (278) mg is reacted with HCl gas and 1 equivalent of ethanol (46 mg) in THF to give an iminoester intermediate. The iminoester is reacted in the same mixture with 1 mmol of ethanediol [HO—$CH_2$—$CH_2$—OH] (62 mg) to give the cyclic orthorethylester Fmoc-NH—CH2-C[O—($CH_2$)$_2$—O]—OEt. Alternatively, 1 mmol of Fmoc-NH—$CH_2$—C($OCH_3$)$_3$ (356 mg) prepared in Example 8 is reacted with 1 mmol of ethanediol [HO—$CH_2$—$CH_2$—OH] (62 mg) in anhydrous THF in presence of 0.1 mmol of p-toluensulfonic acid (19 mg) to give the cyclic orthoethylester Fmoc-NH—$CH_2$—C[O—($CH_2$)$_2$—O]—$OCH_3$.

Example 12

On-resin Preparation of Fmoc-Glycine Cyclic Orthoethylthioloester Resin

On-resin preparation of Fmoc-Glycine cyclic orthoethylthioloester resin is conducted as follows. 10 mmol of Fmoc-NH—$CH_2$—C[O—($CH_2$)$_2$—O]—O—$CH_3$ (3.54 g) prepared in Example 11 is admixed with 1 mmol of $AlCl_3$ (133 mg) in 12 ml of DCM and is reacted with 1 mmol of thiol resin prepared as in Example 9 to achieve thiol exchange (Feugeas et al., Lab. Syn. Org. B., Fac. Sci. Marseilles, Fr. C.R. Acad. Sci., Paris Ser. C. (1968) 266(20): 1506–1507) and generate Fmoc-Glycine cyclic orthoethylthioloester thioester-generating resin. Alternatively, 10 mmol of the Fmoc-NH—$CH_2$—C[O—($CH_2$)$_2$—O]—O—$CH_3$ (3.54g) is admixed with 1 mmol of $SnCl_4$ (260 mg) in 12 ml of dichloroethane and is reacted with 1 mmol of thiolo resin prepared in Example 9 to achieve thiol exchange (Honma et al. Chem. Pharm. Bull. (1976) 24(4): 818–820) and generate Fmoc-Glycine cyclic orthoethylthioloester thioester-generating resin.

Example 13

Solution Phase Preparation of Fmoc-Glycine Cyclic Orthoethylthioloester Acid Bzl-protected Fmoc-Glycine cyclic orthoethylthioloester is prepared in solution as follows. Fmoc-NH—$CH_2$—C[O—($CH_2$)$_2$—O]—O—$CH_3$ (1 mmol (354 mg)) is reacted with HS—$CH_2$—$CH_2$—$CH_2$—COO-Bzl ester (1 mmol 196 mg) in the presence of $AlCl_3$ (0.1 mmol 133 mg) and 2 ml of DCM to achieve thiol exchange (Feugeas et al., Lab. Syn. Org. B., Fac. Sci. Marseilles, Fr. C.R. Acad. Sci., Paris Ser. C. 1968, 266(20):1506–1507), which yields the Bzl-protected Fmoc-Glycine cyclic orthoethylthioloester (Fmoc-NH—$CH_2$—C[O—($CH_2$)$_2$—O]—S—$CH_2$—$CH_2$—COO-Bzl in solution. The same compound also is made by reacting Fmoc-NH—$CH_2$—C[O—($CH_2$)$_2$—O]—O—$CH_3$ (1 mmol 354 mg) with HS—$CH_2$—$CH_2$—$CH_2$—COO-Bzl ester (1 mmol 196 mg) in the presence of $SnCl_4$ (0.1 mmol 26 mg) in 2 ml of dichloethane to achieve thiol exchange (Honma et al. Chem. Pharm. Bull. (1976) 24(4): 818–820) and generate the compound Fmoc-NH—$CH_2$—C[O—($CH_2$)$_2$—O]—S—$CH_2$—$CH_2$—$CH_2$—COO-Bzl.

To remove the benzyl protecting group, reductive cleavage by H2/Pt is employed ("Protecting Groups in Organic Synthesis," 3$^{rd}$ Edition, T. W. Green and P. G. M. Wuts, Eds., John Wiley & Sons, New Tork, N.Y., 1992, pp 250–252; and "Protecting Groups," P. J. Kocienski, Ed., Georg Thieme Verlag, Stuttgart, Germany, 1994, pg. 137). 1 mmol of the Bzl-protected Fmoc-NH—$CH_2$—C[O—($CH_2$)$_2$—O]—S—$CH_2$—$CH_2$—$CH_2$—COO-Bzl compound is dissolved in anhydrous methanol 10 ml and treated at room temperature for 3 hrs with $H_2$ over 100 mg of Pt catalyst to yield the product Fmoc-NH—$CH_2$—C[O—($CH_2$)$_2$—O]—S—$CH_2$—$CH_2$—$CH_2$—COOH. The Fmoc-Glycine cyclic orthoethylthioloester acid is utilized for solution phase coupling, or is attached to a $NH_2$-Rink resin using standard HBTU/DIEA coupling protocol to generate a Fmoc-Glycine cyclic orthoethylthioloester thioester-generating resin.

Example 14

Fmoc SPPS of Peptide on Fmoc-Glycine Orthodimethylthioloester Thioester-generating Resin Fmoc-Glycine orthodimethylthioloester thioester-generating resin prepared in Example 9 is used to synthesize peptide of the sequence FKLAG following standard Fmoc SPPS procedures. Fmoc deprotection is accomplished using 20% Piperidine in DMF (2 times 3 minutes each, per cycle). Chain assembly is performed using standard HBTU/DIEA activation which is 2.1 mmol of Fmoc amino acid, 3.8 ml of 0.5M solution of HBTU in DMF and 1 ml of DIEA, and 1 minute of pre-activation and 30 minutes reaction time for each coupling cycle. The peptide-resin was washed with DMF after the deprotection and coupling reaction steps.

Example 15

Acid Cleavage of FKLAG Peptide from Orthodimethylthioloester Thioester-generating Resin The FKLAG-thioester peptide is generated by acid cleavage of the resin-linked peptide of Example 14. 350 mg of this resin is treated with 5 ml TFA, 0.2 ml water and 0.25 ml thioanisole for 2 hrs. The TFA is evaporated in vacuo and the desired peptide-thioester is precipitated using ethyl ether. The cleavage product comprising the FKLAG-thioester is purified by HPLC and on analysis by electrospray mass spectrometry has the calculated mass, within experimental error.

Example 16

Thioester-mediated Ligation of Orthodimethylthioloester-generated FKLAG-Thioester Peptide to an N-terminal Cysteine-peptide The FKLAG-thioester peptide prepared in Example 15 is ligated to a N-terminal cysteine containing peptide CARHTVHQRHLFG. Approximately 0.3 mg of the FKLAG-thioester peptide and 0.6 mg of N-terminal cysteine peptide CARHTVHQRHLFG, are admixed with 0.25 ml of 6Molar Guanidinium Buffer pH 7 and 0.02 ml of thiophenol at room temperature, and the reaction allowed to proceed overnight. The reaction is analyzed by HPLC and the ligation product is characterized by electrospray mass spectrometry and is found to have the expected mass within experimental error.

Example 17

Fmoc SPPS of Peptide on Fmoc-Glycine Cyclic Orthoethylthioloester Thioester-generating Resin Fmoc-Glycine cyclic orthoethylthioloester thioester-generating resin prepared in Example 12 is used to synthesize peptide of the sequence FKLAG following standard Fmoc SPPS procedures. Fmoc deprotection is accomplished using 20% Piperidine in DMF (2 times 3 minutes each, per cycle). Chain assembly is performed using standard HBTU/DIEA activation which is 2.1 mmol of Fmoc amino acid, 3.8 ml of 0.5M solution of HBTU in DMF and 1 ml of DIEA, and 1 minute of pre-activation and 30 minutes for coupling cycle. Intermediate washes of the peptide-resin are performed using DMF.

Example 18

Acid Cleavage of FKLAG Peptide from Cyclic Orthoethylthioloester Thioester-generating Resin The FKLAG-thioester peptide is generated by acid cleavage of the resin-linked peptide of Example 17. 350 mg of this resin is treated with 5 ml TFA, 0.2 ml water and 0.25 ml thioanisole for 2 hrs at room temperature. The TFA is evaporated in vacuo and the desired peptide-thioester is precipitated using ethyl ether. The cleavage product comprising the FKLAG-thioester peptide is purified by HPLC and on analysis by electrospray mass spectrometry is found to have the expected mass within experimental error.

Example 19

Thioester-mediated Ligation of Cyclic Orthoethylthioloester Generated FKLAG-thioester Peptide to N-terminal Cysteine-peptide The FKLAG-thioester peptide prepared in Example 18 is ligated to a N-terminal cysteine containing peptide CARHTVHQRHLFG as follows. Approximately 0.3 mg of the FKLAG-thioester peptide and 0.6 mg of N-terminal cysteine peptide CARHTVHQRHLFG, are admixed with 0.25 ml of 6Molar Guanidinium Buffer pH 7 and 0.02 ml of thiophenol at room temperature, and the reaction allowed to proceed overnight at room temperature. The reaction is analyzed by HPLC and the ligation product is characterized by electrospray mass spectrometry.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A nucleophile-stable carboxyester thiol of the formula X—C(O)—O—CH(R")—(CH$_2$)$_n$—S—R'", where X is a target molecule of interest comprising an amine protected with one or more nucleophile-labile protecting groups, R" is hydrogen or a non-nucleophile stable group, n is 1 or 2, and R'" is hydrogen, a protecting group, or an acid-, reductive-, or light-labile linker attached to a resin or protecting group that is removable under non-nucleophilic conditions.

2. The nucleophile-stable carboxyester thiol of claim 1, wherein said amine is present on a moiety selected from the group consisting of an amino acid, peptide and polypeptide.

3. The nucleophile-stable carboxyester thiol of claim 1, wherein said nucleophile-cleavable protecting group is Fmoc.

4. The nucleophile-stable carboxyester thiol of claim 1, wherein R" is selected from the group consisting of hydrogen, methyl, aliphatic, branched aliphatic, heteroatom, carbonyl, benzyl, substituted benzyl, nitrile, sulfoxy, and sulfone.

5. The nucleophile-stable carboxyester thiol of claim 1, wherein R'" is selected from the group consisting of hydrogen, aryl, benzyl, and alkyl.

6. The nucleophile-stable carboxyester thiol of claim 1, wherein R" or R'" is covalently attached to a nucleophile-stable linker.

7. The nucleophile-stable carboxyester thiol of claim 6, wherein said linker is covalently attached to a nucleophile-stable resin.

8. A nucleophile-stable thioester-generating resin comprising a carboxyester thiol.

9. The nucleophile-stable thioester-generating resin of claim 8, which comprises the formula X—C(O)—O—CH(R")—(CH$_2$)$_n$—S-linker-resin or X—C(O)—O—CH(R"-linker-resin)-(CH$_2$)$_n$—S—R'", where X is a target molecule of interest comprising one or more nucleophile-labile protecting groups, R" is hydrogen or a non-nucleophile stable group, n is 1 or 2, and R'" is hydrogen, protecting group or an acid, reductive, or light labile linker attached to a resin or protecting group that is removable under non-nucleophilic conditions, and where said linker and resin are nucleophile-stable.

10. A nucleophile-stable carboxyester thiol of the formula X—C(O)—O—CH(R")—(CH$_2$)$_n$—S—R'", where X is a target molecule of interest comprising one or more nucleophile-labile protecting groups, R" is hydrogen or a non-nucleophile stable group, n is 1 or 2, and R'" is hydrogen, a protecting group, or an acid-, reductive-, or light-labile linker attached to a resin or protecting group that is removable under non-nucleophilic conditions, wherein said nucleophile-labile protecting group is Fmoc.

11. The nucleophile-stable carboxyester thiol of claim 10 wherein the target molecule of interest X comprises an amine present on a moiety selected from the group consisting of an amino acid, peptide and polypeptide.

12. The nucleophile-stable carboxyester thiol of claim 10, wherein R" is selected from the group consisting of hydrogen, methyl, aliphatic, branched aliphatic, heteroatom, carbonyl, benzyl, substituted benzyl, nitrile, sulfoxy, and sulfone.

13. The nucleophile-stable carboxyester thiol of claim 10 wherein R'" is selected from the group consisting of hydrogen, aryl, benzyl, and alkyl.

14. The nucleophile-stable carboxyester thiol of claim 10, wherein R" or R'" is covalently attached to a nucleophile-stable linker.

15. The nucleophile-stable carboxyester thiol of claim 14, wherein said linker is covalently attached to a nucleophile-stable resin.

16. A nucleophile-stable carboxyester thiol of the formula X—C(O)—O—CH(R")—(CH$_2$)$_n$—S—R'", where X is a target molecule of interest comprising one or more nucleophile-labile protecting groups, R" is hydrogen or a non-nucleophile stable group, n is 1 or 2, and R'" is hydrogen, a protecting group, or an acid-, reductive-, or light-labile linker attached to a resin or protecting group that is removable under non-nucleophilic conditions, wherein R" is covalently attached to a nucleophile-stable linker, and wherein the linker is covalently attached to a nucleophile-stable resin.

17. The nucleophile-stable carboxyester thiol of claim 16 wherein the target molecule of interest X comprises an amine present on a moiety selected from the group consisting of an amino acid, peptide and polypeptide.

18. The nucleophile-stable carboxyester thiol of claim 16 wherein R" is selected from the group consisting of hydrogen, methyl, aliphatic, branched aliphatic, heteroatom, carbonyl, benzyl, substituted benzyl, nitrile, sulfoxy, and sulfone.

19. The nucleophile-stable carboxyester thiol of claim 16, wherein R'" is selected from the group consisting of hydrogen, aryl, benzyl, and alkyl.

20. A nucleophile-stable carboxyester thiol of the formula X—C(O)—O—CH(R")—(CH$_2$)$_n$—S—R'", where X is a target molecule of interest comprising one or more nucleophile-labile protecting groups, R" is hydrogen or a non-nucleophile stable group, n is 1 or 2, and R'" is hydrogen, a protecting group, or an acid-, reductive-, or light-labile linker attached to a resin or protecting group that is removable under non-nucleophilic conditions, wherein R'" is covalently attached to a nucleophile-stable linker, and wherein the linker is covalently attached to a nucleophile-stable resin.

21. The nucleophile-stable carboxyester thiol of claim 20 wherein the target molecule of interest X comprises an amine present on a moiety selected from the group consisting of an amino acid, peptide and polypeptide.

22. The nucleophile-stable carboxyester thiol of claim 20, wherein R" is selected from the group consisting of hydrogen, methyl, aliphatic, branched aliphatic, heteroatom, carbonyl, benzyl, substituted benzyl, nitrile, sulfoxy, and sulfone.

23. The nucleophile-stable carboxyester thiol of claim 20, wherein R'" is selected from the group consisting of hydrogen, aryl, benzyl, and alkyl.

* * * * *